US00PP16808P2

(12) United States Plant Patent
Verwer

(10) Patent No.: US PP16,808 P2
(45) Date of Patent: Jul. 11, 2006

(54) ***DAHLIA* PLANT NAMED 'GALLERY SISLEY'**

(50) Latin Name: *Dahlia hybrida*
Varietal Denomination: Gallery Sisley

(75) Inventor: Aad W. M. Verwer, Lisse (NL)

(73) Assignee: Verwer Dahlia's B.V., Lisse (NL)

( * ) Notice: Subject to any disclaimer, the term of this patent is extended or adjusted under 35 U.S.C. 154(b) by 16 days.

(21) Appl. No.: 11/119,046

(22) Filed: Apr. 30, 2005

(51) Int. Cl.
*A01H 5/00* (2006.01)

(52) U.S. Cl. ..... Plt./321

(58) Field of Classification Search ..... Plt./321
See application file for complete search history.

*Primary Examiner*—Kent Bell
(74) *Attorney, Agent, or Firm*—C. A. Whealy

(57) ABSTRACT

A new and distinct cultivar of *Dahlia* plant named 'Gallery Sisley', characterized by its compact and rounded plant habit; freely branching growth habit; dark green-colored leaves; early and freely flowering habit; decorative inflorescence form; large inflorescences with red purple-colored ray florets; and good postproduction longevity and garden performance.

2 Drawing Sheets

Botanical designation: *Dahlia hybrida.*
Cultivar denomination: 'Gallery Sisley'.

BACKGROUND OF THE INVENTION

The present Invention relates to a new and distinct cultivar of *Dahlia* plant, botanically known as *Dahlia hybrida* and hereinafter referred to by the name 'Gallery Sisley'.

The new *Dahlia* is a product of a planned breeding program conducted by the Inventor in Lisse, The Netherlands. The objective of the breeding program is to create new potted *Dahlia* cultivars with compact plant habit, freely branching growth habit, early and freely flowering habit, decorative inflorescence form, attractive ray floret coloration, and good postproduction longevity and garden performance.

The new *Dahlia* originated from a cross-pollination made by the Inventor during 2000 of the *Dahlia* cultivar Gallery Monet, disclosed in U.S. Plant Pat. No. 12,284, as the female, or seed, parent with the *Dahlia* cultivar Gallery Art Nouveau, disclosed in U.S. Plant Pat. No. 11,314, as the male, or pollen, parent. The new *Dahlia* was discovered and selected by the Inventor as a single flowering plant within the progeny of the stated cross-pollination grown in a controlled environment in Lisse, The Netherlands, during the summer of 2001. The selection of this plant was based on its unique ray floret coloration.

Asexual reproduction of the new *Dahlia* by cuttings was first conducted in Lisse, The Netherlands during the spring of 2001. Asexual reproduction by cuttings has shown that the unique features of this new *Dahlia* are stable and reproduced true to type in successive generations.

SUMMARY OF THE INVENTION

The cultivar Gallery Sisley has not been observed under all possible environmental conditions. The phenotype may vary somewhat with variations in environment such as temperature and light intensity without, however, any variance in genotype.

The following traits have been repeatedly observed and are determined to be the unique characteristics of 'Gallery Sisley'. These characteristics in combination distinguish 'Gallery Sisley' as a new and distinct *Dahlia* cultivar:

1. Compact and rounded plant habit.
2. Freely branching growth habit.
3. Dark green-colored leaves.
4. Early and freely flowering habit.
5. Decorative inflorescence form.
6. Large inflorescences with red purple-colored ray florets.
7. Good postproduction longevity and garden performance.

Plants of the new *Dahlia* differ primarily from plants of the female parent, the cultivar Gallery Monet, in the following characteristics:

1. Plants of the new *Dahlia* flower earlier than plants of the cultivar Gallery Monet.
2. Plants of the new *Dahlia* are more freely flowering than plants of the cultivar Gallery Monet.
3. Plants of the new *Dahlia* have smaller inflorescences than plants of the cultivar Gallery Monet.
4. Plants of the new *Dahlia* have red purple-colored ray florets whereas plants of the cultivar Gallery Monet have pink and white bi-colored ray florets.

Plants of the new *Dahlia* differ primarily from plants of the male parent, the cultivar Gallery Art Nouveau, in the following characteristics:

1. Plants of the new *Dahlia* are shorter than plants of the cultivar Gallery Art Nouveau.
2. Plants of the new *Dahlia* have smaller inflorescences than plants of the cultivar Gallery Art Nouveau.
3. Plants of the new *Dahlia* and the cultivar Gallery Art Nouveau differ in inflorescence form and ray floret coloration.

Plants of the new *Dahlia* can be compared to plants of the cultivar Melody Lizza, not patented. In side-by-side comparisons conducted in Lisse, The Netherlands, plants of the new *Dahlia* differed from plants of the cultivar Melody Lizza in the following characteristics:

1. Plants of the new *Dahlia* were more compact than plants of the cultivar Melody Lizza.
2. Plants of the new *Dahlia* flowered earlier than plants of the cultivar Melody Lizza.
3. Plants of the new *Dahlia* were more freely flowering than plants of the cultivar Melody Lizza.
4. Plants of the new *Dahlia* had smaller inflorescences than plants of the cultivar Melody Lizza.

BRIEF DESCRIPTION OF THE PHOTOGRAPHS

The accompanying colored photographs illustrate the overall appearance of the new *Dahlia* showing the colors as true as it is reasonably possible to obtain in colored reproductions of this type. Colors in the photographs may differ from the color values cited in the detailed botanical description which accurately describe the colors of the new *Dahlia*.

The photograph on the first sheet comprises a side perspective view of a typical flowering plant of 'Gallery Sisley' grown in a container.

The photograph on the second sheet is a close-up view of typical inflorescences and leaves of 'Gallery Sisley'.

DETAILED BOTANICAL DESCRIPTION

In the following description, color references are made to The Royal Horticultural Society Colour Chart, 1995 Edition, except where general terms of ordinary dictionary significance are used. The aforementioned photographs and the following observations and measurements describe plants grown and flowered during the summer and early autumn in Lisse, The Netherlands, in an outdoor nursery and under conditions which approximate those generally used in commercial production. During the production of the plants, day temperatures ranged between 15 and 30° C. and night temperatures ranged between 10 and 20° C. Plants were pinched one time about three to four weeks after planting rooted cuttings. Plants were about four months old when the photographs and the description were taken.

Botanical classification: *Dahlia hybrida* cultivar Gallery Sisley.

Parentage:

*Female, or seed, parent.*—*Dahlia hybrida* Gallery Monet, disclosed in U.S. Plant Pat. No. 12,284.

*Male, or pollen, parent.*—*Dahlia hybrida* Gallery Art Nouveau, disclosed in U.S. Plant Pat. No. 11,314.

Propagation:

*Type.*—By vegetative cuttings.

*Time to initiate roots.*—Summer and winter: About 5 days at 17° C.

*Time to produce a rooted young plant.*—Summer: About 14 days at 17° C. Winter: About 17 days at 17° C.

*Root description.*—Fine, fibrous and well-branched; older roots, fleshy.

*Tuber description.*—Shape: Fusiform. Clump diameter: About 25 cm. Color: Close to 199C.

Plant description:

*Appearance.*—Perennial decorative-type potted *Dahlia*. Compact and rounded plant habit; upright and somewhat outwardly spreading. Freely branching habit, about eight basal branches each with about four to six lateral branches develop after pinching; dense and full plants. Vigorous growth habit.

*Plant height.*—About 25 cm.

*Plant diameter.*—About 25 cm.

*Lateral branch description.*—Length: About 20 cm. Diameter: Towards base: About 6 mm. Towards apex: About 2 mm. Internode length: About 2 to 4 cm. Strength: Strong. Texture: Glabrous, smooth. Color: 146C; towards the apex, blushed with 166A.

*Foliage description.*—Arrangement: Leaves opposite; leaves may be single or compound with three or five leaflets. Shape: Ovate. Apex: Acuminate. Base: Attenuate. Margin: Serrate; sinuses divergent. Length: Single leaves: About 4 cm. Compound leaves with three leaflets: About 10 cm. Compound leaves with five leaflets: About 12 cm. Width: Single leaves: About 3 cm. Compound leaves with three leaflets: About 8 cm. Compound leaves with five leaflets: About 9 cm. Venation pattern: Pinnate. Texture, upper and lower surfaces: Smooth, glabrous. Color: Developing foliage, upper surface: 146A. Developing foliage, lower surface: 147B. Fully expanded foliage, upper surface: 137A. Fully expanded foliage, lower surface: 148B. Venation, upper surface: 148A. Venation, lower surface: 146A. Petiole length: Single leaves: About 8 mm. Compound leaves with three leaflets: About 1.1 cm. Compound leaves with five leaflets: About 2.5 cm. Petiole diameter: About 2 mm. Petiole color, upper surface: 59B. Petiole color, lower surface: 146C blushed with 59B.

Inflorescence description:

*Appearance.*—Decorative inflorescence form; inflorescences roughly hemispherical in profile. Inflorescences borne on terminals, arising from leaf axils, positioned just above the foliage. Ray and disc florets develop acropetally on the receptacle. Inflorescences not fragrant. Inflorescences persistent.

*Flowering response.*—Flowering recurrent to continuous during the summer and autumn in The Netherlands. Plants start flowering about 55 days after planting.

*Postproduction longevity.*—On the plant, inflorescences maintain good color and substance for about 15 days in an outdoor environment. As cut flowers, inflorescences maintain good color and substance for about five days in an indoor environment.

*Quantity of inflorescences per flowering stem.*—About five open inflorescences and about five inflorescence buds per flowering stem; about 40 inflorescences and inflorescence buds per plant.

*Inflorescence size.*—Diameter: About 9 cm. Depth (height): About 5 cm. Diameter of disc: About 2.4 cm. Receptacle diameter: About 1.4 cm. Receptacle height: About 1.1 cm.

*Inflorescence buds.*—Length: About 1 cm. Diameter: About 1.3 cm. Shape: Oblate. Color: 158A, towards the base, 144A.

*Ray florets.*—Length, fully developed: About 3.5 cm. Width, fully developed: About 1.4 cm. Orientation: Initially upright, outer florets perpendicular to the peduncle to somewhat reflexed. Shape: Ovate. Aspect: Longitudinal axis concave; apex recurved. Apex: Rounded or acute. Base: Attenuate. Margin: Entire. Texture, upper and lower surfaces: Smooth, glabrous; satiny. Number of ray florets per inflorescence: About 120 arranged in about 15 rows. Venation pattern: Parallel. Color: When opening, upper surface: 61A. When opening, lower surface: Towards the apex, 61A; mid-section, 64A; towards the base, 2C. Fully opened, upper surface: Towards the apex; close to 70B; mid-section, 155C overlain with 70B; towards the base, 1A. Fully opened, lower surface: Towards the apex and mid-section, 64A; towards the base, 155C.

*Disc florets.*—Number of disc florets per inflorescence: About 20. Shape: Tubular, elongated. Apex: Five-pointed. Base: Fused. Length: About 1.3 cm. Width: About 0.1 to 0.7 mm. Color: Immature: 160A. Mature: Apex: 21A. Mid-section: 160A. Base: 151A.

*Phyllaries.*—Quantity: One whorl with about five phyllaries. Shape: Roughly ovate. Apex: Rounded. Base: Attenuate. Margin: Entire. Length: About 1.1 cm. Width: About 6 mm. Texture, upper and lower surfaces: Smooth, glabrous. Color, upper surface: 146A. Color, lower surface: 146C.

*Peduncles.*—Length: About 8 cm. Diameter: About 2 mm. Angle: Erect. Strength: Strong. Texture: Glabrous, smooth. Color: 151A blushed with 166A.

*Reproductive organs.*—Androecium: Present on disc florets only. Stamen quantity: About five per floret. Anther shape: Linear. Anther length: About 2 mm. Anther color: 17A. Pollen amount: Scarce. Pollen color: 17B. Gynoecium: Present on both ray and disc florets. Pistil quantity: One per floret. Pistil length: About 4 mm. Stigma shape: Lanceolate. Stigma color: 13B. Style length: About 3 mm. Style color: 150B. Ovary color: 9C.

*Seed.*—Seed development has not been observed.

Disease/pest resistance: Resistance to pathogens and pests common to *Dahlias* has not been observed on plants grown under commercial greenhouse or outdoor conditions.

Weather tolerance: Plants of the new *Dahlia* have been observed to be very tolerant to wind, rain and full sun conditions. Plants of the new *Dahlia* have been observed to tolerate temperatures from 0 to 40° C.

It is claimed:

1. A new and distinct cultivar of *Dahlia* plant named 'Gallery Sisley', as illustrated and described.

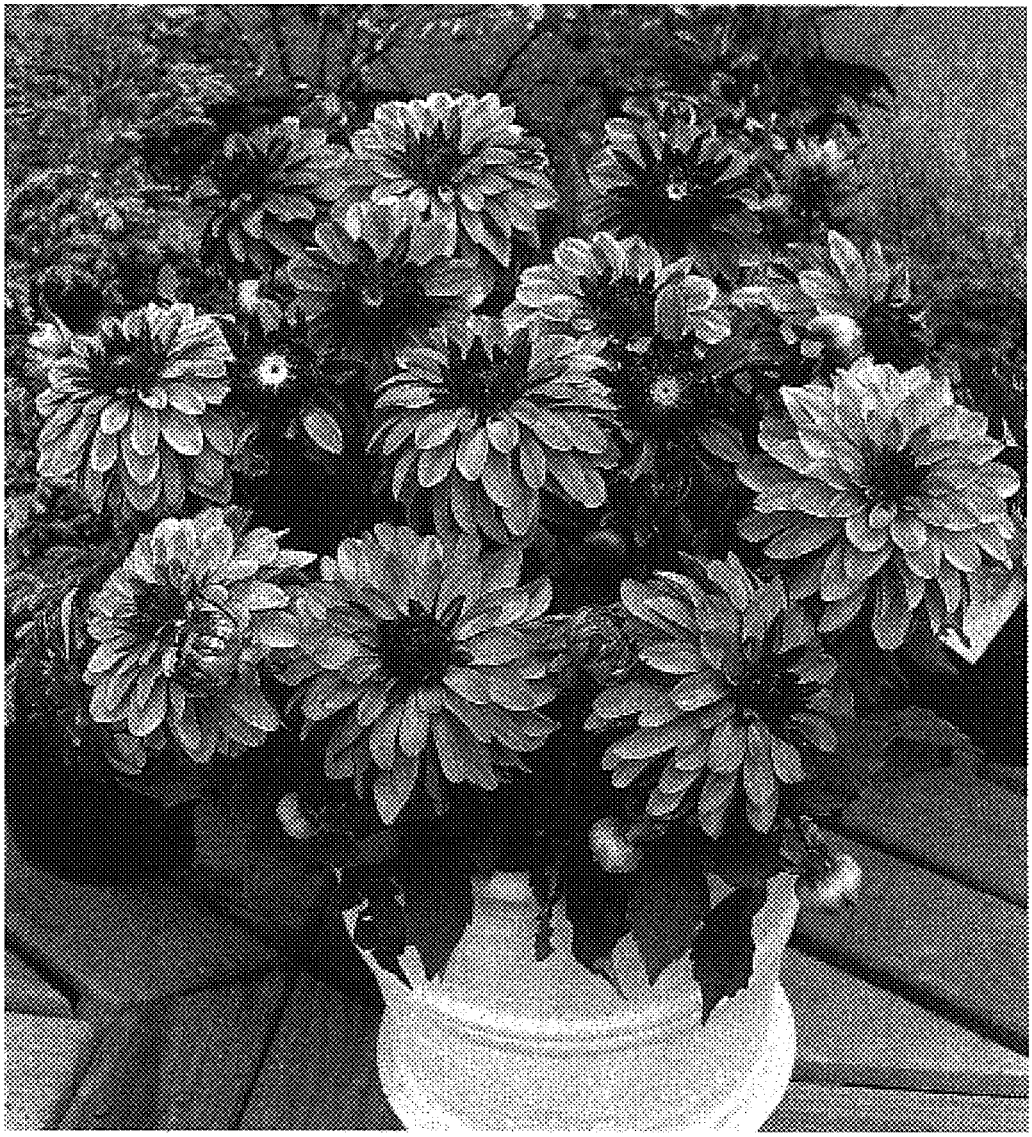

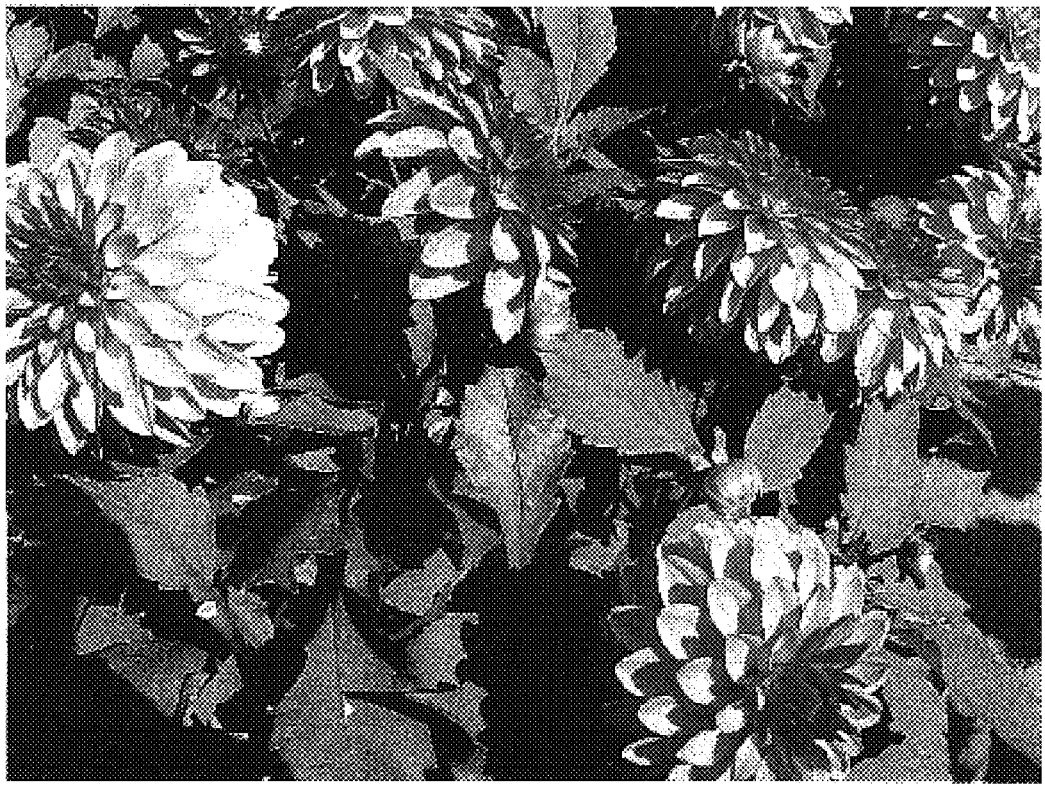

* * * * *